(12) United States Patent
Ahlering et al.

(10) Patent No.: US 9,089,315 B1
(45) Date of Patent: Jul. 28, 2015

(54) METHODS AND DEVICES FOR ADJUNCTIVE LOCAL HYPOTHERMIA

(75) Inventors: Thomas E. Ahlering, Laguna Niguel, CA (US); David S. Finley, Long Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 969 days.

(21) Appl. No.: 12/874,141

(22) Filed: Sep. 1, 2010

Related U.S. Application Data

(60) Provisional application No. 61/239,330, filed on Sep. 2, 2009.

(51) Int. Cl.
| | |
|---|---|
| *A61B 18/02* | (2006.01) |
| *A61M 25/10* | (2013.01) |
| *A61F 7/12* | (2006.01) |
| *A61B 18/00* | (2006.01) |

(52) U.S. Cl.
CPC ....... *A61B 18/02* (2013.01); *A61B 2018/00023* (2013.01); *A61F 7/12* (2013.01); *A61F 7/123* (2013.01); *A61M 25/1011* (2013.01)

(58) Field of Classification Search
USPC .......................................... 606/20–27, 34, 41
See application file for complete search history.

(56) References Cited

U.S. PATENT DOCUMENTS

| | | | | |
|---|---|---|---|---|
| 4,519,390 | A * | 5/1985 | Horne | 606/15 |
| 5,431,648 | A * | 7/1995 | Lev | 606/27 |
| 5,496,271 | A * | 3/1996 | Burton et al. | 607/27 |
| 6,611,699 | B2 * | 8/2003 | Messing | 600/372 |
| 6,976,492 | B2 * | 12/2005 | Ingle et al. | 128/898 |
| 2002/0151887 | A1 * | 10/2002 | Stern et al. | 606/41 |
| 2005/0154383 | A1 * | 7/2005 | Koop et al. | 606/9 |

OTHER PUBLICATIONS

Finley, David S. et al., "Hypothermic nerve-sparing radical prostatectomy . . . ," Urology, Sep. 2008, pp. 1-6.

* cited by examiner

*Primary Examiner* — Michael Peffley
*Assistant Examiner* — Daniel Fowler
(74) *Attorney, Agent, or Firm* — Venable LLP; Stefan J. Kirchanski

(57) ABSTRACT

Devices and methods for using adjunctive cooling to promote recovery of function following pelvic surgery include a uretral catheter and a cryogenic cautery device. A system for producing chilled irrigation fluid recirculates the chilled fluid through a catheter inserted into the patients urethra to provide a low temperature during and following surgery. A surgical cautery device is equipped with cryogenic emitters which spray cryogenic fluid on the cautery site prior to and/or following thermal cautery to reduce inflammation and related damage from such cauterization. The various embodiments are advantageously used together.

1 Claim, 3 Drawing Sheets

METHODS AND DEVICES FOR ADJUNCTIVE LOCAL HYPOTHERMIA

CROSS REFERENCE

This application is a Non-Provisional of and claims the benefit under 35 U.S.C. §119(e) of U.S. Provisional Application Ser. No. 61/239,330, filed Sep. 2, 2009 of which is entirely incorporated herein by reference.

GOVERNMENT FUNDING

Not applicable.

BACKGROUND OF THE INVENTION

It has generally been appreciated in the art that lowering the temperature of body tissues can limit trauma due to surgery. The present inventors have been involved in using cooling to prevent collateral damage during prostate surgery through the use of an endorectal cooling system (ECB). Their original system included intracorporeal cooling irrigation as an adjunct to endorectal cooling, to induce local hypothermia of the pelvis during radical prostatectomy (and other laparoscopic/robotic procedures) to reduce inflammation and neuromuscular injury and thereby to promote functional recovery outcomes (urinary and sexual function after radical prostatectomy). The cold irrigation creates an additive effect to the endorectal cooling to enhance cooling, clears the operative field of blood to improve visualization, and reduces thermal spread and minimizes collateral injury when using thermal electrocautery for hemostasis; this is particularly important when performing the nerve sparing part of the operation where one tries to minimize damage to the delicate neurovascular bundles. We demonstrated a statistically significant faster rate of continence recovery with hypothermia. This work represented the first ever application of hypothermia to radical prostatectomy. The research manuscript which has now been published in Urology, 2009 Feb. 26, notes, "Adjunctive."

The present invention concerns cooling of surrounding tissues prior to surgery. A modified Foley catheter is described for providing urethral cooling during and after prostate or other surgery of the urogenital system. Cooling of the urethra is achieved by circulating chilled fluid through a coiled capillary tube that is in contact with the catheter's wall. This cools the urethra as well as urethral sphincter. Additional cooling can be provided by circulating the chilled fluid within the bladder. An improved cautery instrument is also disclosed. This system is a normal cautery instrument equipped with cryogenic emitters disposed about the tips. A blast of cryogenic fluid is emitted just prior to energizing the cauterizing tip to lower the temperature of the tissue to be cauterized.

SUMMARY OF THE INVENTION

Lowering the temperature of tissue before and during a surgery can limit collateral damage resulting from the surgery. We developed a general cooling system to test our concepts. A specific implementation of our devices is a cooling urethral catheter for use during prostate surgery and for other surgery of the male urogenital system. The catheter is a modified Foley catheter that can be inserted through the urethra and anchored in the bladder. A capillary tube accepts refrigerated liquid and conducts it to the distal end of the catheter to cool the catheter walls and urethral tissue. A return path for the cooling fluid is provided by the main body of the catheter. The distal tip of the catheter which extends into the patient's bladder is provided with two rather than one eyelet as in a traditional catheter. This allows the catheter to also be used to circulate cooling fluid within the patent's bladder to further cool surrounding tissues.

In spite of tissue cooling effected by the catheter and by local irrigation with chilled fluid, the use of cautery instruments to cut the tissue can still result in temperature increases and collateral damage. To solve this problem we provide a special cooled cautery instrument. The single or dual cauterizing and cutting blade of a cautery instrument are provided with a plurality of cryogenic emitters that surround the blade(s). Prior to and following the cauterizing operation, the emitters spray cryogenic fluid on the tissue surface immediately proximal to the blades. This results in rapid local cooling that counteracts collateral damage caused by the cautery instrument.

BRIEF DESCRIPTION OF THE DRAWINGS

FIG. 3 is a diagram of a device for providing cryogenic cooling to a cauterizing instrument.

DESCRIPTION OF THE INVENTION

The present invention encompasses additional cooling methods to augment the cooling provided in our original endorectal cooling system where 4° C. sterile water intracorporeal irrigation was used to augment cooling of the ECB. With ECB only, the median temperature was 28.30° C. (range 17.5°-35.4° C., standard deviation [SD] 3.54, 95% confidence interval [CI] 1.04). When adjunctive cold irrigation was used, the median temperature decreased to 25.10° C. (range 18.0°-30.0° C., SD 2.93, CI 0.86; P=0.0001)."

Figure 1:
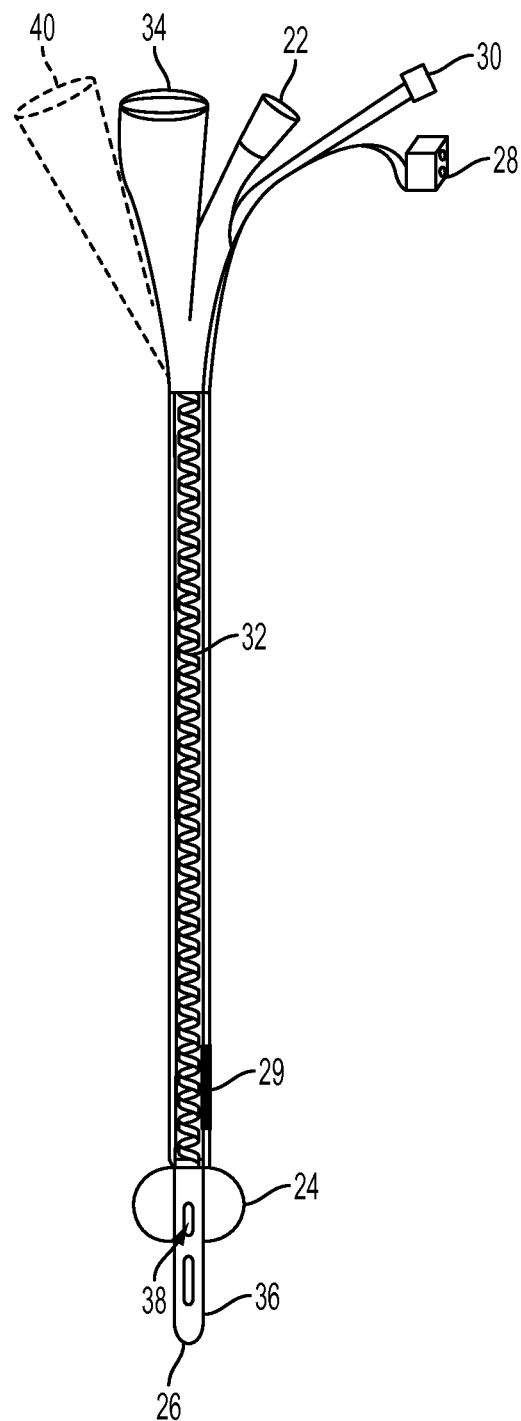
FIG. 1 is a diagram of a device according to the present invention for providing intra-urethral cooling.
Figure 2:
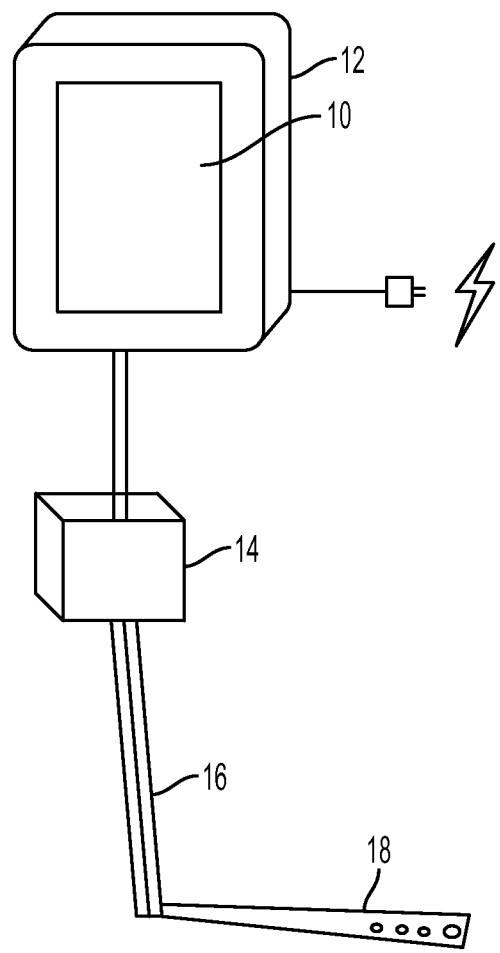
FIG. 2 is a diagram of a simple system for providing adjunctive cooling.

Our initial test of cold laparoscopic irrigation (as shown in FIG. 2) used a setup consisting of a 3 L bag of cold sterile water 10 (chilled by overnight placement in a freezer 12) attached to a Bard Davol suction irrigation pump. Irrigation tubing 16 conducted the liquid to an irrigation tip 18. We had difficulty keeping the bag of saline cold enough and had to use foam insulation. Following disclosure of our work to the Innercool Company, that company developed a commercial version which is called "Urochill." This is a system for supplying cold irrigation by using a small coil type heat-exchanger that is used in conjunction with Innercool's existing chilling console.

Advantages of Adjunctive cold irrigation—The cold irrigation creates an additive effect to the endorectal cooling to enhance cooling, clear the operative field of blood to improve visualization, and reduce thermal spread and minimize collateral injury when using thermal electrocautery for hemostasis; this is particularly important when performing the nerve sparing part of the operation where one tries to minimize damage to the delicate neurovascular bundles. We demonstrated a statistically significant faster rate of continence recovery with hypothermia. Overall temperatures were lower with endorectal cooling and irrigation combined than with endorectal cooling alone.

A second embodiment of the present invention is a more direct cooling of the urethra. It is generally held that intrinsic urinary sphincteric deficiency (ISD) and detrusor over-activity are primarily responsible for post-prostatectomy urinary incontinence. We previously demonstrated statistically significant faster rates of continence recovery with hypothermia. Additional cooling strategies are beneficial to augment our current strategies of inducing local hypothermia. Specifically, bladder cooling may be more directly impacted by intravesical (intracavitary) cooling. Additional direct cooling of the urethral sphincter with a cooled catheter cools from inside the urethral lumen to allow for more effective intraoperative cooling and especially post-operative cooling. Current endorectal cooling can only be performed during the operation and possibly for as much as 6 hours post-operatively because the patient needs to ambulate to minimize the risk of blood clot formation in the legs. Intravesical and direct urethral cooling would augment the process by allowing longer periods of cooling. For example, intravesical cooling could be done during the immediate post-operative period (i.e., 24 hours) whereas urethral cooling with a cooled catheter could continue for the duration (usually 7 days) of catherization.

Intravesical and urethral cooling can be accomplished by running cold irrigation by gravity or pump through a three way Foley catheter as shown in FIG. 2. The catheter 22 has a balloon port 22 for inflating a retention balloon 24 to retain the tip 26 of the device within the bladder. A thermistor feed 28 connects to a thermistor 29 to allow monitoring of internal temperature. An inflow port 30 conducts cold fluid through a microcapillary tube 32 that coils around the inside surface of the catheter body to chill it. The chilled water is released into the lumen of the catheter near the balloon 24 and exits through a drainage lumen 34. The drainage eyelet 36 of the catheter also connects to the lumen. The optional second eyelet 38 connects to the optional third port 40 for circulating fluid through the bladder to achieve continuous bladder irrigation (CBI).

This ultimately would also keep the catheter itself cold which would directly cool the urethra and sphincter complex to minimize edema and inflammation. There is some basic evidence in animal models that cooling of the spinal cord can suppress reflex urinary incontinence in animals with induced bladder hyper-reflexia (Callsen-Cencic 1999). Alternatively, one can create a urethral catheter that becomes cool without cycling fluid into the bladder. The catheter could contain a separate lumen or cooling coil in a closed loop fashion. The advantage is direct cooling of the bladder and urethra from the inside rather than from the outside of the structures. This results in more effective reduction in edema and inflammation resulting in more pronounced functional recovery. Additionally the patient can have this cooling for a prolonged period of time after the operation which is not possible with endorectal cooling.

Figure 3A:
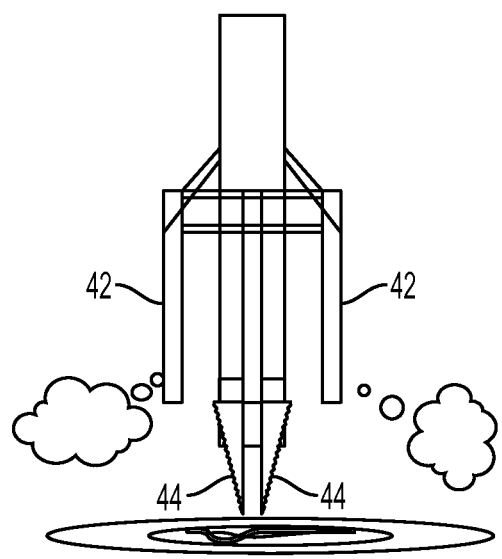
FIG. 3A shows a side view and FIG. 3B shows a view from below the device).
Figure 3B:
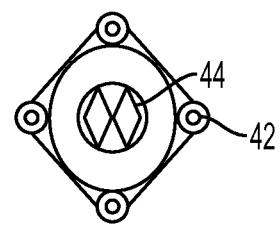

A third embodiment is preemptive local cooling for cautery. The spread of thermal energy to surrounding tissue during monopolar and bipolar cautery causes direct thermal cellular injury and secondary inflammatory damage leading to unintentional ischemia and apoptosis of nearby tissues. Preemptive lowering of non-target tissue temperature just prior to activating cautery confers a protective benefit preventing this "collateral damage" to neuromuscular tissues (i.e., cavernous neurovascular bundles). Inflammatory damage can lead to downstream delay of recovery of potency and continence. This "Cooltip" technology is shown diagrammatically in FIG. 3 (FIG. 3A side-view and FIG. 3B end on view) allows for reduction in collateral non-target thermal injury. A burst of compressed cryogen (i.e., tetrafluoroethane gas, carbon dioxide or other cryogen) or super cooled mist is released via directed circular array of micro-nozzles (emitters) 42 milliseconds prior to cauterization effected by energizing the cauterizing tip 44 thereby creating a cooled protective zone around the cautery tip. Different array configurations can be available for different instruments (i.e., monopolar scissors versus bipolar scissor, hook, etc.). Micro-capillary tubing supplies the cryogen by plugging into the instrument body and attaching to a pressurized supply tank of cryogen. Although optimal results result from applying the cryogen prior to the cauterizing, application immediately following the cauterizing treatment can enhance the effectiveness of the treatment. Thus, depending on the exact circumstances, pulses of cryogenic fluid are applied prior to thermal cautery and/or following thermal cautery.

What is claimed is:

1. An improved catheter for lowering the temperature of the urethra and optionally the bladder comprising;
    a catheter portion for insertion into a urethra with a distal tip thereof entering a bladder, the catheter portion having ports at a proximal end;
    an inflatable balloon disposed near the distal tip for anchoring the catheter portion in the bladder;
    a capillary tube disposed within the catheter portion and coiling around a surface thereof for carrying cooling fluid from one of the ports to the tip of the catheter portion where the cooling fluid is released into a lumen of the catheter portion;
    a drainage port in fluidic communication with the lumen whereby cooling fluid is circulated through the catheter portion to cool the urethra when cooling fluid is withdrawn through the drainage port; and
    at least two eyelets disposed near the distal tip within the bladder when the catheter is inserted, one eyelet in fluidic communication with the lumen and one eyelet in fluidic communication with a bladder circulation port whereby cooling fluid is circulated within the bladder when cooling fluid is withdrawn through the bladder circulation port.

* * * * *